US009932486B1

(12) United States Patent
Cogar et al.

(10) Patent No.: US 9,932,486 B1
(45) Date of Patent: Apr. 3, 2018

(54) COALESCENT AND NON-IONIC SURFACTANT BLEND

(71) Applicant: Eastman Chemical Company, Kingsport, TN (US)

(72) Inventors: Jennifer Lynn Cogar, Unicoi, TN (US); Damon Ray Billodeaux, Longview, TX (US); Jerome Leonard Stavinoha, Jr., Longview, TX (US); Michelle Nicole Tuttle, Hallsville, TX (US)

(73) Assignee: Eastman Chemical Company, Kingsport, TN (US)

( * ) Notice: Subject to any disclaimer, the term of this patent is extended or adjusted under 35 U.S.C. 154(b) by 3 days.

(21) Appl. No.: 15/285,770

(22) Filed: Oct. 5, 2016

(51) Int. Cl.

| | |
|---|---|
| ***C08K 5/10*** | (2006.01) |
| ***C08K 5/101*** | (2006.01) |
| ***C07C 69/67*** | (2006.01) |
| ***C09D 7/12*** | (2006.01) |
| ***C09D 121/02*** | (2006.01) |
| ***C08L 31/00*** | (2006.01) |

(52) U.S. Cl.
CPC ............ *C09D 7/1233* (2013.01); *C07C 69/67* (2013.01); *C08K 5/10* (2013.01); *C08L 31/00* (2013.01); *C09D 7/1216* (2013.01); *C09D 121/02* (2013.01)

(58) Field of Classification Search
USPC ..................................... 524/308, 310; 560/1
See application file for complete search history.

(56) References Cited

U.S. PATENT DOCUMENTS

| | | | | |
|---|---|---|---|---|
| 7,101,930 B2 * | 9/2006 | Martin | C08F 8/00 | 428/411.1 |
| 2014/0079888 A1 * | 3/2014 | Teng | C09D 133/12 | 427/393.6 |
| 2014/0242403 A1 * | 8/2014 | Olsen | C09D 5/1637 | 428/497 |

FOREIGN PATENT DOCUMENTS

JP 56030948 A 3/1981

OTHER PUBLICATIONS

Materna et al., C12 Hydroxyester ethoxylates as nonionic surfactants, Central European Journal of Chemistry, Apr. 2011, 4 page Context, Downloaded on Dec. 1, 2017.*

ASTM D2244-16; Standard Practice for Calculation of Color Tolerances and Color Differences from Instrumentally Measured Color Coordinates.

ASTM D2354-10$^{\epsilon}$1; Standard Test Method for Minimum Film Formation Temperature (MFFT) of Emulsion Vehicles.

ASTM D2486-06; Standard Test Method for Scrub Resistance of Wall Paints.

ASTM D4838-88; Standard Test Method for Determining the Relative Tinting Strength of Chromatic Paints.

* cited by examiner

*Primary Examiner* — Tae H Yoon
(74) *Attorney, Agent, or Firm* — Matthew W. Smith

(57) ABSTRACT

The invention is comprised of a coalescent and non-ionic surfactant blend additive for use in water-based architectural coating formulations. The dual-function blend is produced by reacting 2,2,4-trimethyl-1,3-pentanediol monoisobutyrate with ethylene oxide in the presence of a basic catalyst and separating the desired ethoxylated coalescent and non-ionic surfactant blend from the reaction product.

7 Claims, 17 Drawing Sheets

COALESCENT AND NON-IONIC SURFACTANT BLEND

FIELD OF THE INVENTION

The invention generally relates to a coalescent and non-ionic surfactant blend. More particularly the invention relates to a coalescent and non-ionic surfactant blend that is a dual-function additive for architectural coatings.

BACKGROUND OF THE INVENTION

Architectural coatings formulators generally utilize discrete coalescing aid and surfactant additives to deliver good performance in common water-based latex paint formulations. Alkyl phenol ethoxylate (APE) has been a primary nonionic surfactant used for many years in latex paint formulation. However, there are environmental and health concerns relating to the use of APE in paint formulations. Various ethoxylated alcohols are possible replacements for traditional APE surfactant technology, however these discrete additives add to the cost of the formulation and increase the complexity and difficulty of adjusting paint formulations. Some of these discrete additives may partially provide both coalescing aid and surfactant functionality, but do not deliver adequate performance in common formulations to allow total replacement of two or more additives with a single additive. Thus there is a need for a single additive for architectural coatings formulation that provides both coalescing aid and surfactant performance.

The additive of the present invention addresses the needs of architectural coatings formulators who seek to simplify complex formulations and reduce manufacturing costs while maintaining paint performance. The present invention addresses this need as well as others, which will become apparent from the following description and the appended claims.

SUMMARY OF THE INVENTION

The invention is as set forth in the appended claims.

There is now provided a dual-function additive for water-based architectural coating formulations that functions as both a coalescent and non-ionic surfactant.

In particular, there is now provided a blend comprising:

a) structure (1);

(1)

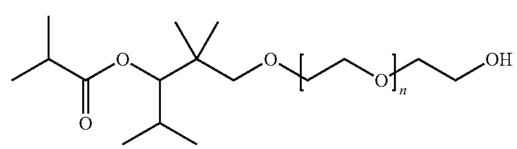

b) structure (2);

(2)

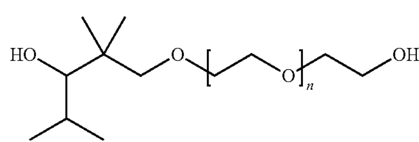

c) c) structure (3); and (3)

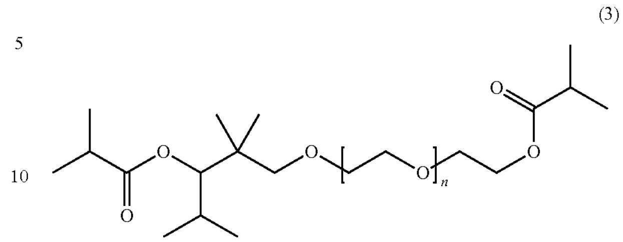

wherein n is 1 to 5.

In another aspect, there is now provided a coating composition comprising:

A. at least one latex compound;

B. at least one pigment;

C. a coalescent and non-ionic surfactant blend comprising:

a) structure (1);

(1)

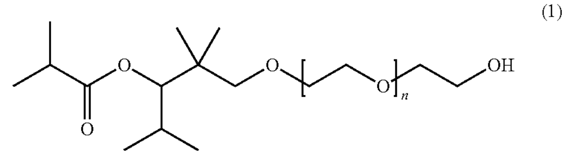

b) structure (2); and (2)

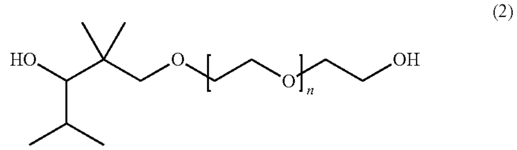

c) structure (3);

(3)

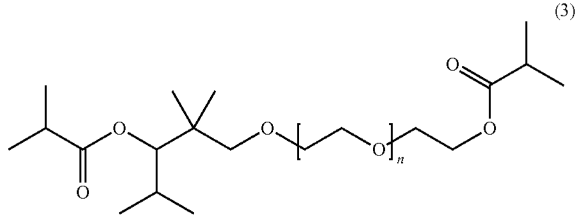

wherein n equals 1 to 5.

The FIGS. 8, 10, 12, 15, 16 and 17 are graphs of Delta E with multiple colorants.

Figure 13:
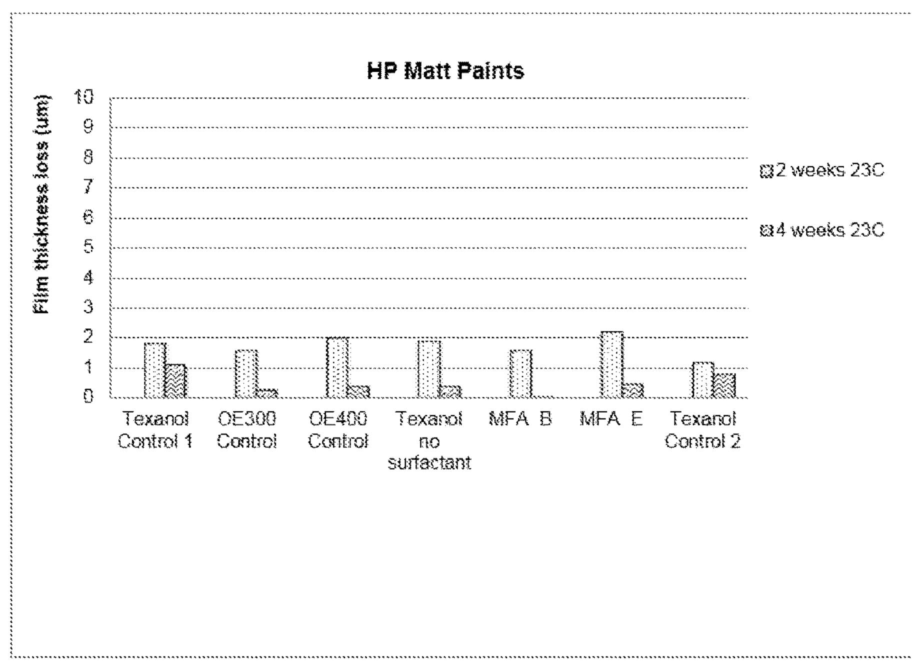
Figure 14:
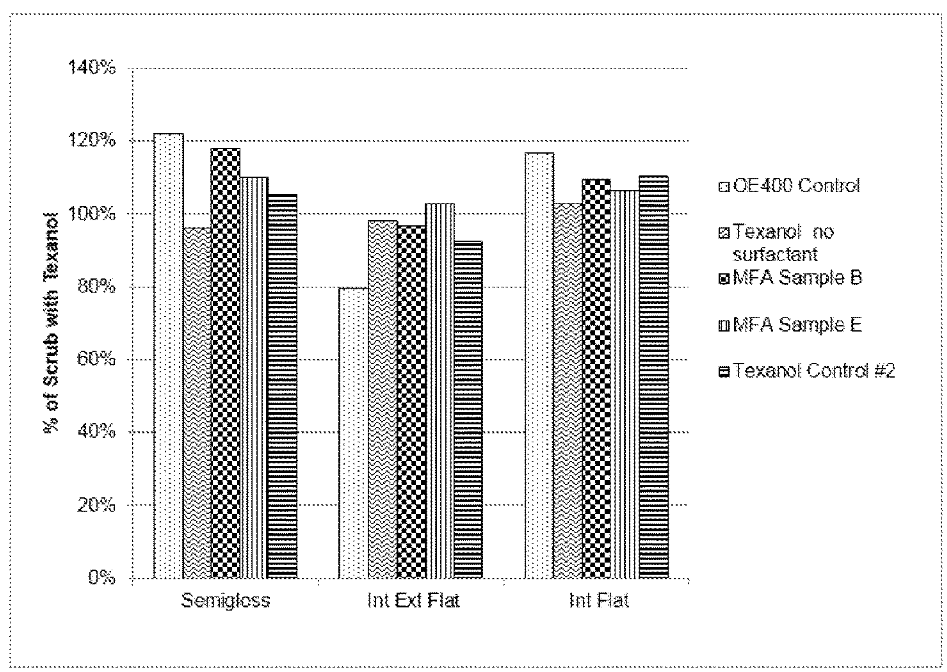

The FIGS. 9, 11, 13, and 14 are graphs of paint film resistance to abrasion with 9, 11, 13 showing thickness loss measurements. FIG. 14 shows the relative number of cycles required to remove the paint film.

DETAILED DESCRIPTION OF THE INVENTION

Unless otherwise indicated, all numbers expressing quantities of ingredients, properties such as molecular weight, reaction conditions, and so forth used in the specification and claims are to be understood as being modified in all instances by the term "about." Unless indicated to the contrary, the numerical parameters set forth in the following specification and attached claims are approximations that may vary depending upon the desired properties sought to be obtained by the present invention. At the very least, each numerical parameter should be construed in light of the number of reported significant digits and by applying ordinary rounding techniques. Further, the ranges stated in this disclosure and the claims are intended to include the entire range specifically and not only the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ alkyl groups" is intended to specifically include and disclose $C_1$ and $C_5$ alkyl groups as well as $C_2$, $C_3$, and $C_4$ alkyl groups.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurements.

As used in the specification and the appended claims, the term "blend" means two or more uniformly dispersed liquid substances.

As used in the specification and the appended claims, the singular forms "a," "an" and "the" include their plural referents unless the context clearly dictates otherwise. In addition, references to a composition containing or including "an" alcohol or "a" surfactant is intended to include other ingredients, in addition to the one named. The terms "containing" or "including" are intended to be synonymous with the term "comprising", meaning that at least the named compound, element, particle, or method step, etc., is present in the composition or article or method, but does not exclude the presence of other compounds, catalysts, materials, particles, method steps, etc., even if the other such compounds, material, particles, method steps, etc., have the same function as what is named, unless expressly excluded in the claims.

Also, it is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

In one aspect of the invention, ethoxylated derivatives of 2,2,4-trimethyl-1,3-pentanediol monoisobutyrate, are a dual-function additive for water-based architectural coatings formulations. The additive delivers coalescing aid and nonionic surfactant performance in a single material without supplemental additions of other discrete coalescing aids and nonionic surfactants.

The present invention provides a blend comprising:

a) structure (1);

(1)

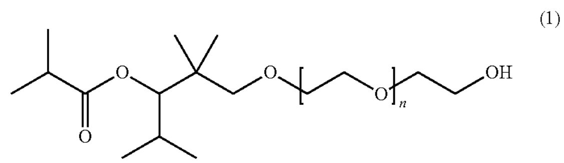

b) structure (2);

(2)

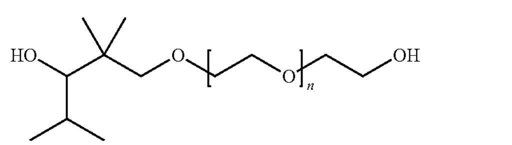

c) c) structure (3); and (3)

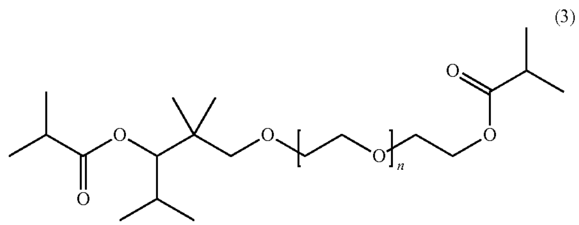

wherein n is 1 to 5.

In one embodiment of the invention, the multifunctional blend of the present invention is produced by reacting 2,2,4-trimethyl-1,3-pentanediol monoisobutyrate (also known as Eastman Texanol™ Ester Alcohol, and TXOL) with ethylene oxide (also known as 1,2-epoxyethane, oxirane, and EO) in the presence of a base catalyst. Although not bound to any particular reaction theory, it is theorized that under reaction conditions TXOL converts to a mixture of TXOL, 2,2,4-trimethyl-1,3-pentanediol (TMPD), and 2,2,4-trimethyl-1,3-pentanediol diisobutyrate (TXIB). The ethoxylation reaction adds a hydrophilic portion to the hydroxyl groups in TXOL and TMPD. In the case of TXIB, since there are no hydroxyl groups for the EO to react with, it is theorized that a transesterification reaction takes place between TXIB and an ethoxylated TXOL molecule generating the ethoxylated TXIB and a TXOL. Additionally, the ethoxylated products can also isomerize. Thus, the ethoxylation reaction product is a mixture of ethoxylate materials represented by structures (1), (2), and (3) where n can equal one to five, along with unreacted starting materials.

In various embodiments of the invention, the ethoxylation process can be carried out in a reactor, such as a batch stirred autoclave, a continuous stirred tank, a plug flow reactor, a trickle bed, or a loop reactor.

In other embodiments of the invention, a catalyst can be used in the ethoxylation process. Suitable catalysts possess alkaline characteristics. The catalyst can be heterogeneous such as a hydrotalcite, calcium oxide, or magnesium oxide.

The catalyst can be homogeneous such as hydroxides of sodium, potassium, cesium, or lithium. The catalyst can be an alkaline or alkaline earth metal salt of an alcohol such as ethanol, propanol, butanol, isobutanol or 2-ethylhexanol. Such salts are commonly referred to as “alkoxides”. The homogeneous catalyst can also be an alkaline or alkaline earth metal salt of 2,2,4-trimethyl-1,3-pentanediol monoisobutyrate or 2,2,4-tri methyl-1,3-pentanediol.

In some embodiments of this invention sufficient ethylene oxide may be used to achieve one to five moles EO per mole of ethoxylate. Higher levels of ethoxylation may be achieved, however as the amount of ethoxylation increases the reaction product becomes more difficult to recover by separation methods such as distillation and form highly colored materials due to excessive heating.

In another embodiment of the invention, the reaction is conducted at temperatures of 100° C. to 200° C. In other embodiments the reaction is conducted at temperatures of 125° C. to 170° C. The reaction is conducted at pressures such that the ethylene oxide is kept in the liquid phase. In some embodiments of the invention the reaction is conducted under pressures of 345 kPa to 1800 kPa. In other embodiments of the invention, the reaction is conducted under pressures of 861 kPa to 1241 kPa.

The crude reactor product can contain disproportionation and trans-esterification products such as isobutanol, 2,4-dimethyl-3-pentanone, and isobutyl butyrate. The raw reactor product can also contain unreacted starting materials. These unreacted starting materials can be separated from the desired multifunctional blend. Any method of separation can be used to separate the desired mixture of ethoxylates from the raw reaction product. Flash distillation, column distillation, cross current extraction, or other methods known to those versed in the art may be used.

In a paint formulation, coalescing aid functionality helps in the formation of the paint film, especially at lower temperatures. The coalescing aid acts as a plasticizer in latex emulsions. The coalescing aid lowers the glass transition temperature (Tg) of the latex polymer. As the paint dries the polymers that have been softened by the coalescing aid are allowed to flow together and form a film after the water has left the system. Nonionic surfactant functionality improves pigment wetting during paint processing and the overall stability of finished water-based latex paints. The nonionic surfactant lowers the interfacial tension between the liquid paint and the substrate as well as between the water in the paint and the dispersed pigment particles. A non-ionic surfactant enhances the mechanical stability and shelf-life of latex paints. Non-ionic surfactant also helps with the stability of the paint during the post-addition of pre-dispersed pigments, during point-of-sale tinting.

The multifunctional blend of the present invention is effective in a variety of latex paint formulations including acrylic, vinyl acrylic, vinyl versatate vinyl acrylics, ethylene vinyl acetate, and styrene acrylic latexes. It also performs with a variety of pigment types such as single pigments or mixtures of pigment types including $TiO_2$, calcium carbonate, talc, silica, nepheline syenite, and clays and with a ratio of pigments to total paint solids of 10% to 85%.

EXAMPLES

Synthesis of Ethoxylated 2,2,4-trimethyl-1,3-pentanediol monoisobutyrate

Example 1

150 g (700 mmol) of 2,2,4-trimethyl-1,3-pentanediol monoisobutyrate (TXOL) containing, 0.25% Na by weight, was placed in a 300 mL stainless steel autoclave. The autoclave was sealed and purged with nitrogen. 20 mL (17.5 g, 400 mmol) of ethylene oxide (EO) was condensed from a sample bomb and pressured into the autoclave with nitrogen. The molar ratio of TXOL to EO was 1.2 mmol of TXOL per mmol of EO. The autoclave was placed into a computer controlled heating and stirring apparatus. The reactor was brought to 125° C. and charged with nitrogen to a pressure of 861.8 kPa. The mixture was stirred at 700 rpm. The apparatus was held at pressure and temperature for 2 hours. The apparatus was cooled in an ice bath to below 10° C., vented, and the contents sampled.

Reactor effluent was subjected to vacuum distillation to produce material for testing. The effluent was charged to a 500 mL round bottom flask with a Vigreux fractionating column, chilled condenser, and fraction collecting vessel. The entire apparatus was placed under 11 torr of vacuum and heated with an electric heating mantle. A base temperature of 230° C. was reached and light materials were removed overhead at 182° C. Heating was discontinued when the base pot temperature began to rise above 230° C. The base material was filtered and used for testing in subsequent examples. The reaction product was analyzed by gas chromatography. A typical product contains 0-5% molecules with n=1, 75-90% molecules with 2 n≤5, and 5-10% molecules with n≥6. Results are presented in Table 1.

Example 2

Example 2 was carried out similarly to Example 1, except with 0.9 mmol of TXOL per mmol of EO.

Examples 3 & 4

Examples carried out in a manner similar to Example 1 with indicated ratio of reactants (Table 1). The 2,2,4-trimethyl-1,3-pentanediol monoisobutyrate used in these examples contained 0.4% Na by weight.

TABLE 1

| Example | TXOL: EO (mol: mol) | EO Conversion | %EO1[a] | %EO2[a] | %EO3[a] | %EO4[a] | %EO5[a] |
|---|---|---|---|---|---|---|---|
| 1 | 1.8 | 88% | 77.7 | 22.2 | 0 | 0 | 0 |
| 2 | 0.87 | 70% | 47.3 | 33.1 | 13.4 | 6.2 | 0 |
| 3 | 2 | 91% | 37.6 | 29.3 | 19.7 | 4.2 | 9.1 |
| 4 | 1.3 | 100% | 29.9 | 30.7 | 18.5 | 11.6 | 9.2 |

[a]mole % of ethoxylates containing 1, 2, 3, 4, or 5 moles of EO.

Example 5

The batch autoclave was modified to allow for constant feed of ethylene oxide into the reactor. The EO sample bomb was connected to an IPSCO model syringe pump. The pump was charged with EO from the bomb. The autoclave was loaded with 100 g of TXOL containing 0.13% Na by weight. The autoclave was brought to 170° C. and 965 kPa with $N_2$. When temperature and pressure were reached, EO was continuously fed into the autoclave at 0.8 mL/min. During EO addition, the autoclave reached a pressure of 1723 kPa. At this point, the feed pump was discontinued and temperature maintained. After 3 hours of total reaction time, the autoclave was cooled, and the contents analyzed by gas chromatography. Approximately 57 g of EO were fed into the unit to give a TXOL:EO ratio of 0.36. Results are presented in Table 2.

Example 6

This example was carried out using the apparatus described in Example 5. The autoclave was loaded with 100 g of TXOL and brought to an operating temperature of 170° C. and pressure of 689 kPa. EO was fed into the reactor at a rate of 0.6 mL/min until a pressure of 1723 kPa was reached. The reaction was allowed to progress for 3 hours. Results are presented in Table 2.

TABLE 2

| Example | EO Feed (mL/min) | TXOL:EO (mol: mol) | EO Conversion | %EO1[a] | %EO2[a] | %EO3[a] | %EO4[a] | %EO5[a] |
|---|---|---|---|---|---|---|---|---|
| 5 | 0.8 | 0.36 | 69% | 21.5 | 32.7 | 22.2 | 14.2 | 9.4 |
| 6 | 0.6 | 0.36 | 66% | 21.4 | 32.2 | 22.2 | 14.7 | 9.5 |

[a]mole % of ethoxylates containing 1, 2, 3, 4, or 5 moles of EO.

Examples 7-9

These examples were carried out as described in Example 6, except the reactor was brought to an operating pressure of 345 kPa before EO was fed at a rate of 6.4 mL/min. The reactions in these examples were carried out at various temperatures as indicated in Table 3.

TABLE 3

| Example | Temperature (° C.) | EO Conversion | %EO1[a] | %EO2[a] | %EO3[a] | %EO4[a] | %EO5[a] |
|---|---|---|---|---|---|---|---|
| 7 | 170 | 70% | 21.2 | 32.1 | 22.4 | 14.7 | 9.5 |
| 8 | 180 | 77% | 18.3 | 29.6 | 22.8 | 15.6 | 13.6 |
| 9 | 160 | 67% | 19.5 | 31.3 | 22.7 | 15.6 | 10.9 |

[a]mole % of ethoxylates containing 1, 2, 3, 4, or 5 moles of EO.

Example 10

The apparatus in Example 5 was utilized. The autoclave was charged with 100 g of TXOL containing 0.24% Na by weight and brought to an operating temperature of 170° C. The reactor was brought to 689 kPa with $N_2$ and EO feed was commenced at 0.5 mL/min. After 3 hours of feed time, the reactor pressure reached 1585 kPa and EO feed was terminated. The reactor was maintained at 170° C. until 5.5 hours had elapsed and the internal pressure had fallen to 1150 kPa. The reactor was cooled and samples were taken from the reaction mixture. Results are shown in Table 4.

TABLE 4

| Example | TXOL Conversion | EO Conversion | %EO1[a] | %EO2[a] | %EO3[a] | %EO4[a] | %EO5[a] |
|---|---|---|---|---|---|---|---|
| 10 | 95% | 38% | 10.1% | 23.6% | 25.7% | 21.5% | 19.2% |

[a]mole % of ethoxylates containing 1, 2, 3, 4, or 5 moles of EO.

The functionality of these ethoxylate blends was tested in a variety of latex types and in several typical paint formulations. Coalescing efficiency was compared to common commercial controls in a variety of latexes. Performance dependent on film formation enhanced by the coalescent and stability and wetting properties generally provided by non-ionic surfactant were compared to control formulations containing common coalescents and non-ionic surfactants. Paints were prepared by replacing both the coalescent and the non-ionic surfactant with the invention ethoxylate blends. The level of ethoxylate blend was based on coalescent required to obtain a targeted Minimum Film Formation Temperature (MFFT) in the latex. The function of a coalescent is to lower the temperature where a latex can form a film thereby reducing the MFFT.

The ethoxylate blends were split to replace the surfactant in the high-shear pigment dispersion phase for pigment wetting and the coalescent in the lower shear letdown phase of the formulation.

Example 11

The ethoxylate blends assist with coalescence in a variety of latex types as evidenced by reduction of latex MFFT with addition of material. The results are shown in FIGS. 1-7. Example 11 demonstrates that the ethoxylate blends act as coalescents (reducing the minimum film formation temperature). FIGS. 1-7 represent results obtained in seven different types of architectural latexes. These include pure acrylics, styrene acrylics, and vinyl acrylics. The data is expressed as the amount of ethoxylated blend of this invention used as a percent of the latex solids (or the phr—parts per hundred resin). MFFT is tested by ASTM D2354. Two versions of the invention ethoxylate blends (MFA B and MFA E) were compared to conventional coalescents, Texanol™ ester alcohol (Texanol), Optifilm™ enhancer 300 (OE300) and, Optifilm™ enhancer 400 (OE 400). The coalescents Texanol™ ester alcohol, Optifilm™ enhancer 300 and, Optifilm™ enhancer 400 are products of Eastman Chemical Company. The results show that the invention ethoxylate blends decrease the MFFT of each of the latexes in a similar way as conventional coalescents.

Examples 12-17 show performance of the invention ethoxylate blends in a variety of paint formulations. Table 5-10 show the different formulations. For Tables 5-7, each table shows the relative quantity of materials used (in grams) and the order the materials were added. The portion labeled "grind" indicates that it was prepared with a high shear disperser with a saw tooth blade. The portion labeled "letdown" was prepared with a low shear mixer and a paddle blade. Tables 8-10 are written in US form which is pounds (lb.) per 100 gallons (gal).

Figure 1:
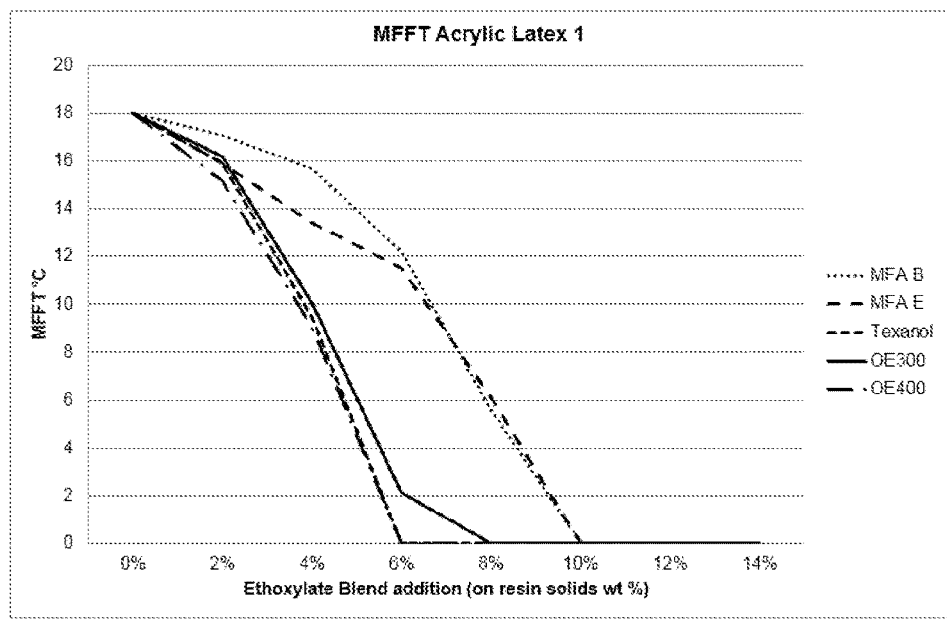
FIGS. 1-7 are graphs of the amount of ethoxylated blend added to latex paints versus the Minimum Film Formation Temperature (MFFT) measured in latex paints.
Figure 2:
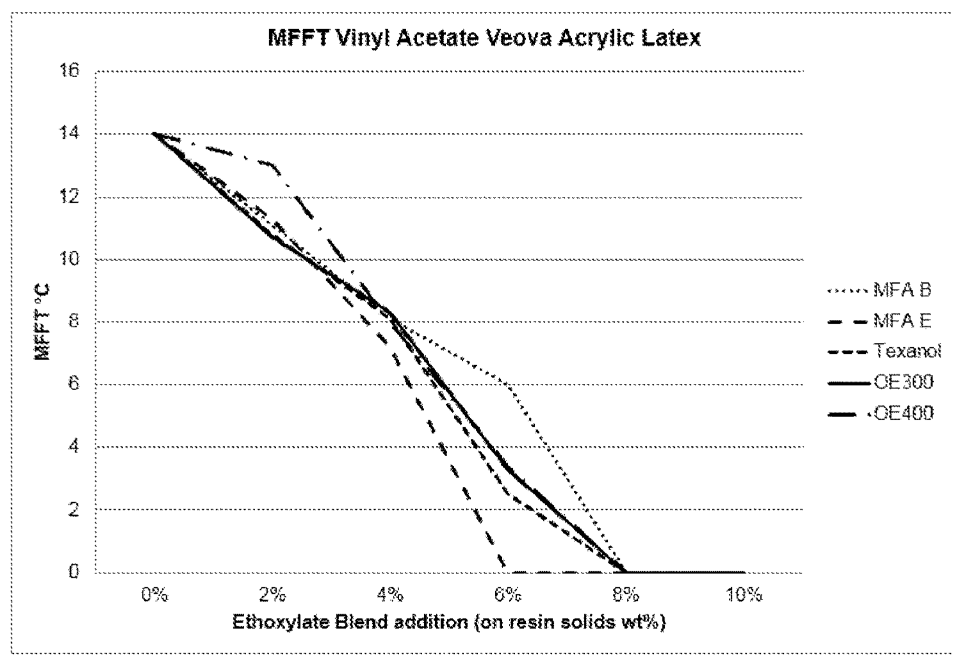
Figure 3:
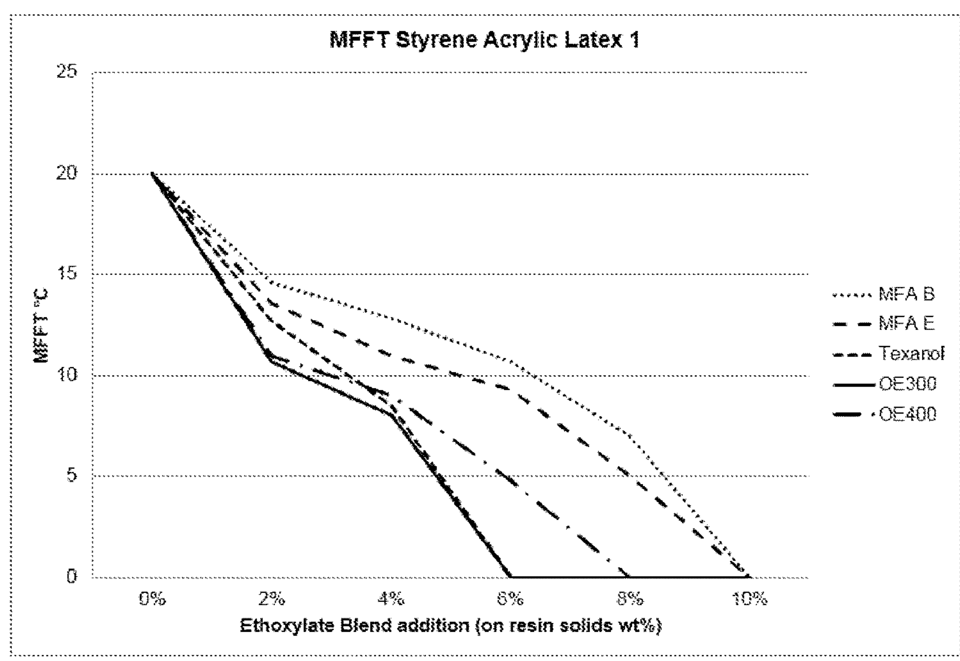
Figure 4:
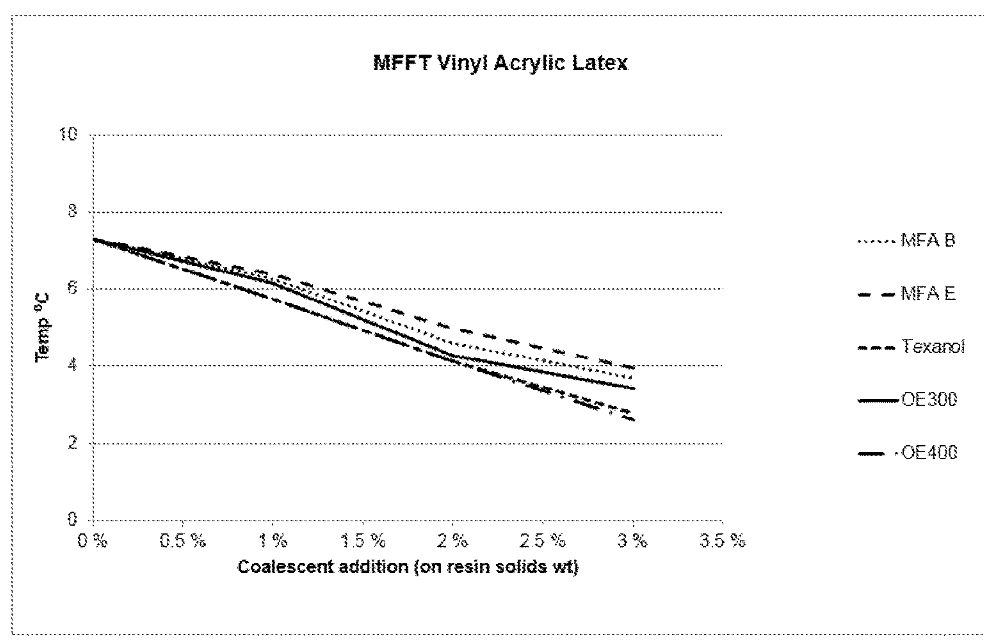
Figure 5:
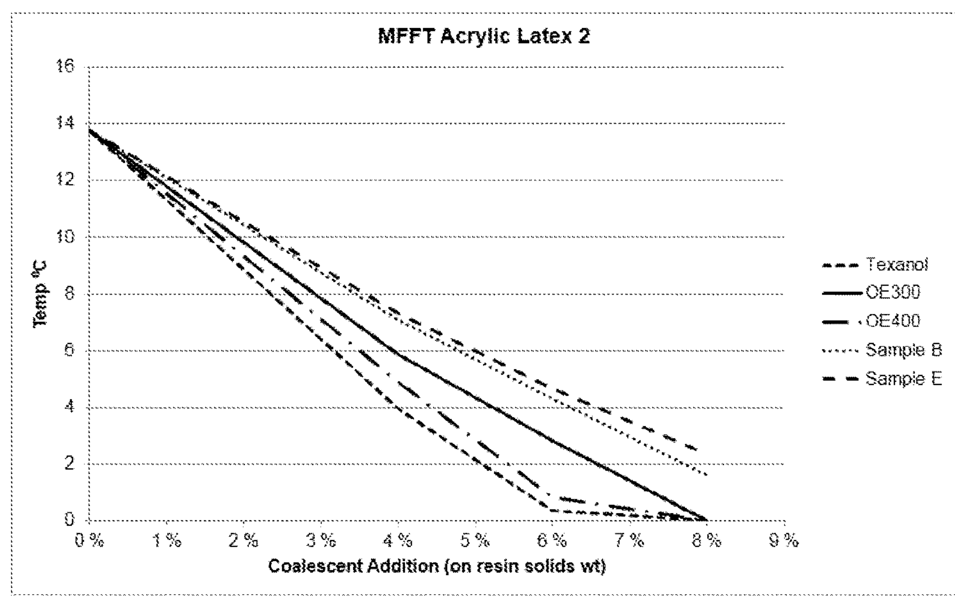
Figure 6:
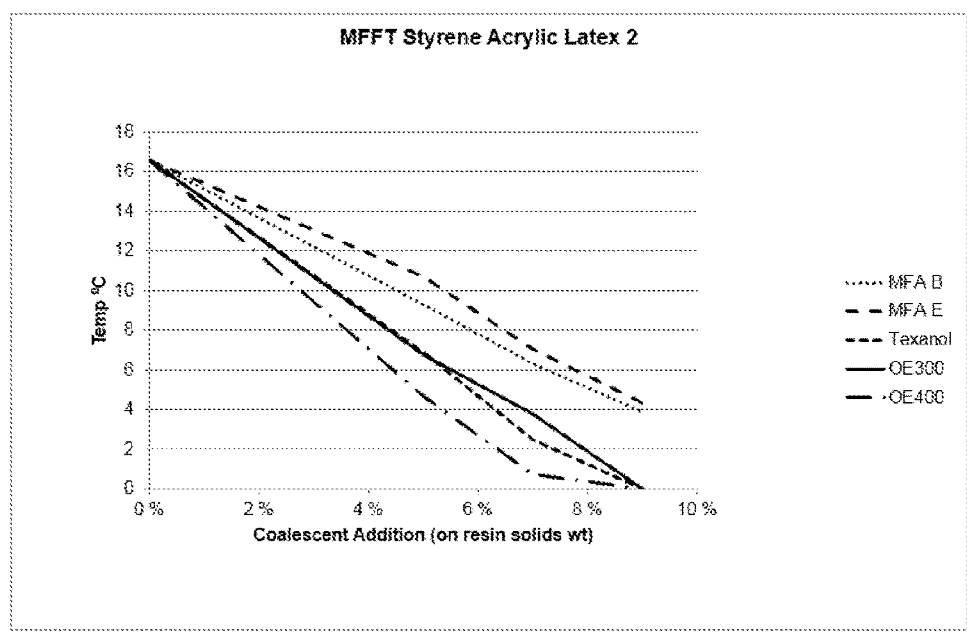
Figure 7:
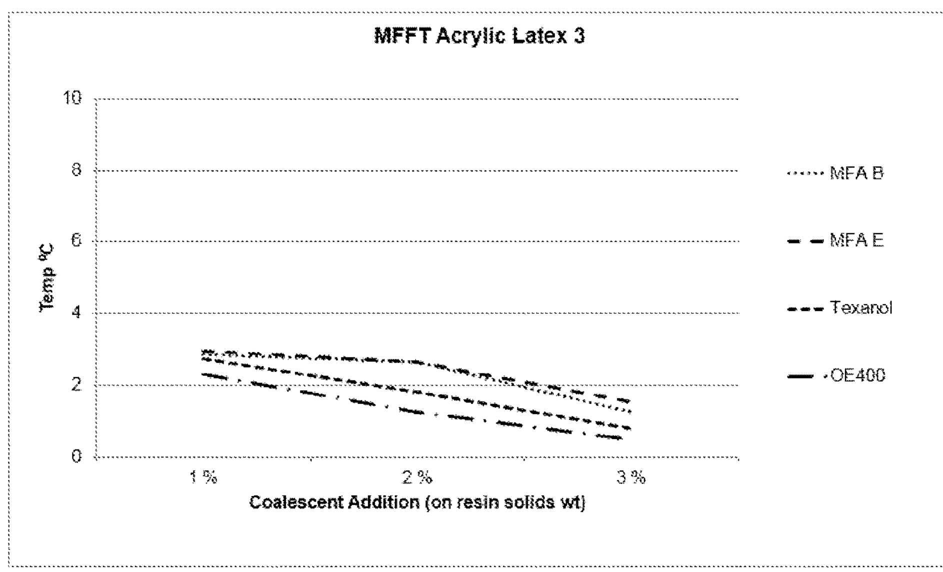
Figure 8:
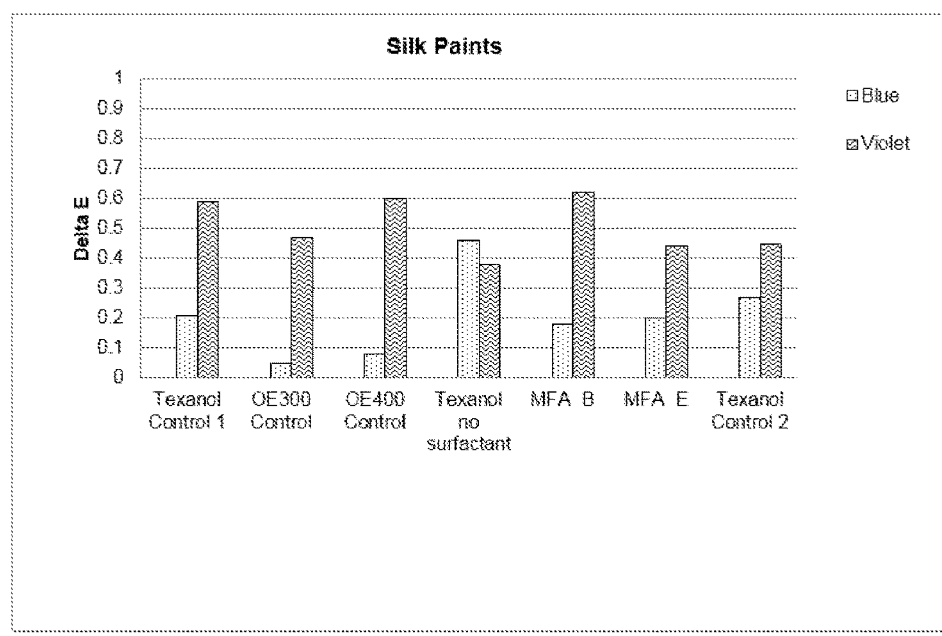
Figure 10:
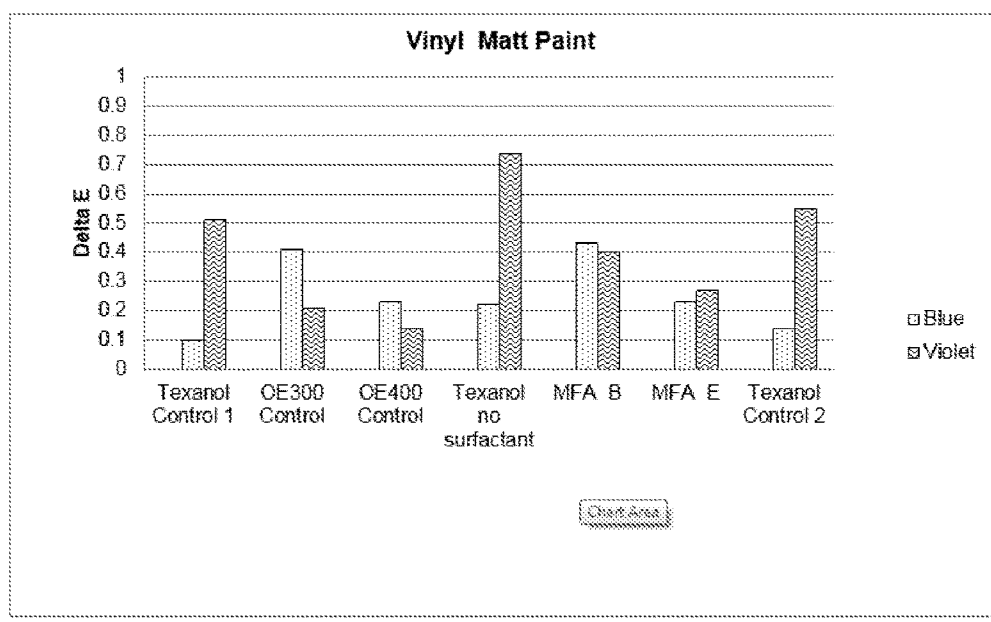
Figure 12:
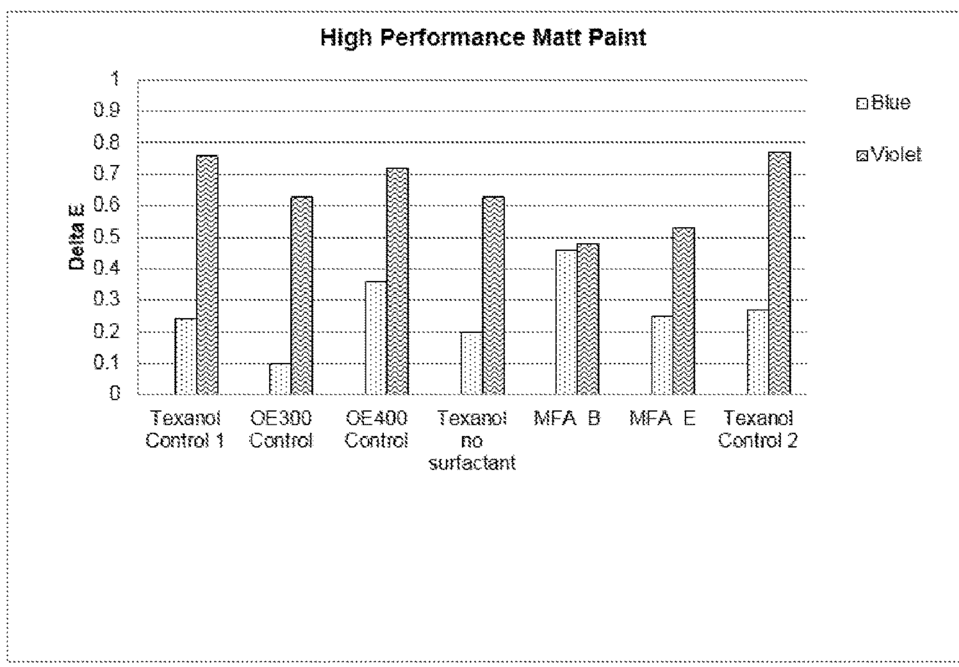

For each formulation, the Figs. show two properties. FIGS. 8, 10, and 12 shows Delta E with multiple colorants. Delta E is the difference in overall color between the control paint and the paints containing the invention ethoxylate blend materials. Delta E is calculated from LAB measurements on a spectrophotometer as described in ASTM D2244. One primary function of a non-ionic surfactant is to enable pre-dispersed colorants to be added to the base paint and develop the appropriate level of color. In this case, Delta E is compared to the control paint that contains both a common coalescent and a common non-ionic surfactant. Delta E of less than 1 indicates that the paint containing the ethoxylate blend of this invention is very similar to the control paint. There is also data representing the control paint (Texanol) with the surfactant removed. In some cases, this shows significantly higher Delta E, again confirming that the ethoxylate blends of this invention are providing surfactant functionality.

Figure 9:
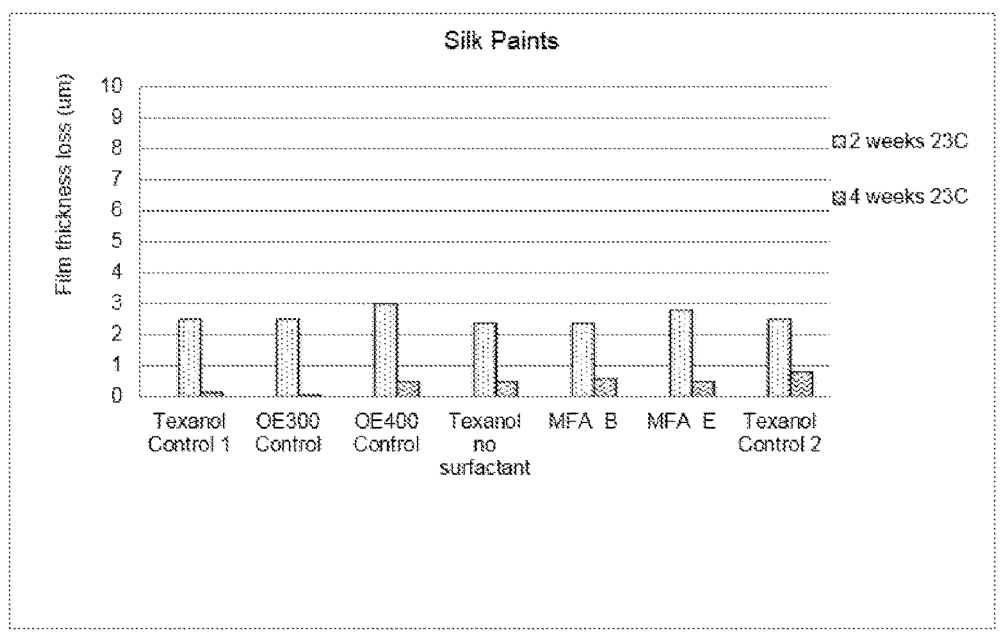
Figure 11:
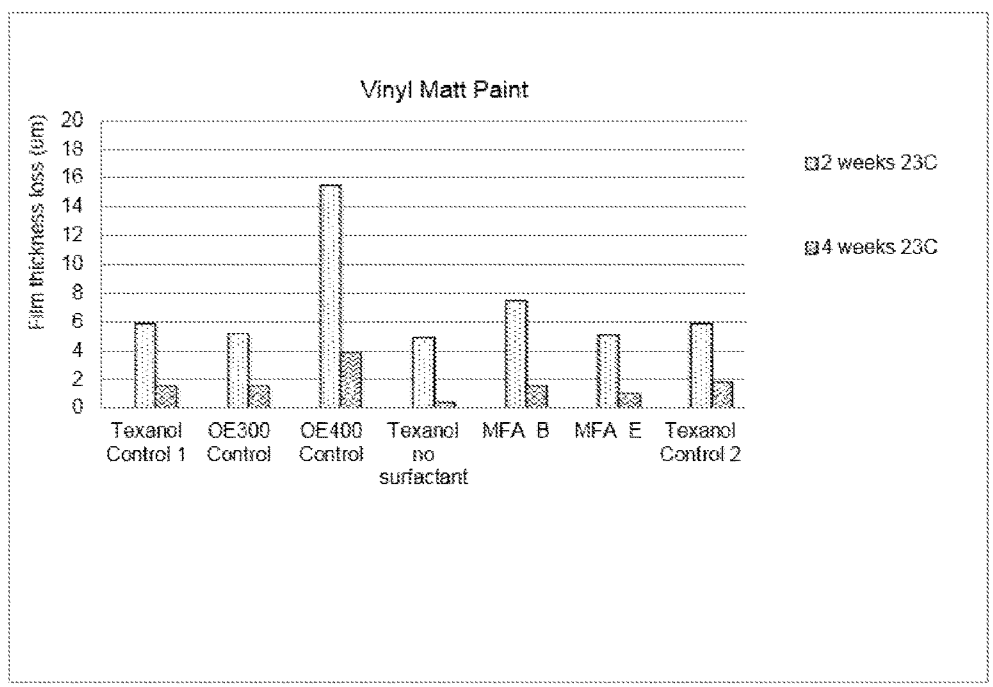

The FIGS. 9, 11 and 13 represents scrub resistance. These tests were done by using ISO Method 11998. Scrub resistance is a key paint property that is impacted by coalescent performance because it improves film formation. Lower film thickness loss indicates good durable films. FIG. 14 shows also scrub resistance results, but tested by a different method, ASTM D2486. This is presented as the percent of the control scrub resistance that is maintained by the experimental paints. It shows the scrub data for three different formulations (Table 8, 9 and 10). Examples 12-17 show that the latex paints containing the invention ethoxylate blends perform similarly to the control latex paints containing conventional separate surfactants and coalescent aids materials.

Example 12: Vinyl Silk Paint

TABLE 5

Grams of Raw Material in Vinyl Silk Paint Formulation

| Raw Material Description | Texanol EA Control Sample | Texanol No Surfactant Sample | Sample #1 MFA B | Sample #2 MFA E |
|---|---|---|---|---|
| Grind | | | | |
| Water | 44.3 | 48.1 | 47.4 | 48.3 |
| Cellulosic Thickener | 1.4 | 1.4 | 1.4 | 1.4 |
| Neutralizing Agent | 0.4 | 0.4 | 0.4 | 0.4 |
| Defoamer | 0.4 | 0.4 | 0.4 | 0.4 |
| Dispersant | 3.5 | 3.5 | 3.5 | 3.5 |
| Non-ionic Surfactant | 3.8 | 0.0 | 0.0 | 0.0 |
| Multi-Functional Additive (MFA B) | 0.0 | 0.0 | 1.9 | 0.0 |
| Multi-Functional Additive (MFA E) | 0.0 | 0.0 | 0.0 | 1.4 |
| Biocide | 0.2 | 0.2 | 0.2 | 0.2 |
| Fine Kaolin extender | 9.0 | 9.0 | 9.0 | 9.0 |
| Pigment | 34.5 | 34.5 | 34.5 | 34.5 |
| Letdown | | | | |
| vinyl acetate/ VeoVa10/acrylate | 77.0 | 77.0 | 77.0 | 77.0 |
| Opaque Polymer | 9.0 | 9.0 | 9.0 | 9.0 |
| Coalescent | 3.2 | 3.2 | 0.0 | 0.0 |
| Multi-Functional Additive (MFA B) | 0.0 | 0.0 | 1.9 | 0.0 |
| Multi-Functional Additive (MFA E) | 0.0 | 0.0 | 0.0 | 1.4 |
| Neutralizing Agent | 1.2 | 1.2 | 1.2 | 1.2 |
| Defoamer | 0.4 | 0.4 | 0.4 | 0.4 |
| Water | 18.3 | 18.1 | 18.3 | 18.3 |
| Total Grams | 206.6 | 206.4 | 206.9 | 206.4 |

The Delta E results of the paint formulations in Table 5 are shown in FIG. 8 and the scrub resistance results of the paint formulations in Table 5 are shown in FIG. 9.

Example 13: Vinyl Matt Paint

TABLE 6

Grams of Raw Material in a Vinyl Matt Paint Formulation

| Raw Material Description | Texanol EA Control Sample | Texanol (no surfactant) Sample | Sample #1 MFA B | Sample #2 MFA E |
|---|---|---|---|---|
| Grind | | | | |
| Water | 52.4 | 52.4 | 52.5 | 52.5 |
| Cellulosic Thickener | 1.6 | 1.6 | 1.6 | 1.6 |
| Neutralizing Agent | 1.4 | 1.4 | 1.4 | 1.4 |
| Defoamer | 0.6 | 0.6 | 0.6 | 0.6 |
| Nonionic surfactant | 1.4 | 0.0 | 0.0 | 0.0 |
| Multi-Functional Additive B | 0.0 | 0.0 | 0.7 | 0.0 |
| Multi-Functional Additive E | 0.0 | 0.0 | 0.0 | 0.6 |
| Dispersant | 1.0 | 1.0 | 1.0 | 1.0 |
| Biocide | 0.5 | 0.5 | 0.5 | 0.5 |
| Calcium/Magnesium Carbonate | 16.8 | 16.8 | 16.8 | 16.8 |
| Talc | 9.8 | 9.8 | 9.8 | 9.8 |
| Flash Calcined Clay | 19.6 | 19.6 | 19.6 | 19.6 |
| Titanium Dioxide | 22.4 | 22.4 | 22.4 | 22.4 |
| Letdown | | | | |
| Styrene Acrylic | 25.8 | 25.8 | 25.8 | 25.8 |
| Coalescent | 0.9 | 0.9 | 0.0 | 0.0 |
| Multi-Functional Additive B | 0.0 | 0.0 | 0.7 | 0.0 |
| Multi-Functional Additive E | 0.0 | 0.0 | 0.0 | 0.6 |
| HASE Thickener | 1.2 | 1.2 | 1.2 | 1.2 |
| Defoamer | 0.6 | 0.6 | 0.6 | 0.6 |
| Neutralizing Agent | 0.4 | 0.4 | 0.4 | 0.4 |
| Water | 37.0 | 37.0 | 34.2 | 34.2 |
| Total Grams | 193 | 192 | 190 | 190 |

The Delta E results of the paint formulations in Table 6 are shown in FIG. 10 and the scrub resistance results of the paint formulations in Table 6 are shown in FIG. 11.

Example 14: High Performance Matt Paint

TABLE 7

Grams of Raw Material in a High Performance Matt Paint

| Raw Material Description | Texanol EA Control Sample | Texanol No Surfactant Sample | Sample #1 MFA B | Sample #2 MFA E |
|---|---|---|---|---|
| Grind | | | | |
| Water | 43.8 | 43.8 | 43.8 | 43.8 |
| Cellulosic Thickener | 1.3 | 1.3 | 1.3 | 1.3 |
| Neutralizing Agent | 0.8 | 0.8 | 0.8 | 0.8 |
| Defoamer | 8.0 | 8.0 | 8.0 | 8.0 |
| Dispersant | 0.9 | 0.9 | 0.9 | 0.9 |
| Non-ionic Surfactant | 1.6 | 0.0 | 0.0 | 0.0 |
| Multi-Functional Additive (MFA B) | 0.0 | 0.0 | 1.5 | 0.0 |
| Multi-Functional Additive (MFA E) | 0.0 | 0.0 | 0.0 | 1.5 |
| Biocide | 0.6 | 0.6 | 0.6 | 0.6 |
| Calcium/Magnesium Carbonate | 19.1 | 19.1 | 19.1 | 19.1 |
| Talc | 9.5 | 9.5 | 9.5 | 9.5 |
| Flash Calcined Clay | 23.9 | 23.9 | 23.9 | 23.9 |
| Titanium Dioxide | 23.0 | 23.0 | 23.0 | 23.0 |

TABLE 7-continued

Grams of Raw Material in a High Performance Matt Paint

| Raw Material Description | Texanol EA Control Sample | Texanol No Surfactant Sample | Sample #1 MFA B | Sample #2 MFA E |
|---|---|---|---|---|
| Letdown | | | | |
| Pure Acrylic Latex | 55.0 | 55.0 | 55.0 | 55.0 |
| Coalescent | 2.0 | 2.0 | 0.0 | 0.0 |
| Multi-Functional Additive | 0.0 | 0.0 | 1.5 | 0.0 |
| Multi-Functional Additive | 0.0 | 0.0 | 0.0 | 1.5 |
| Neutralizing Agent | 0.6 | 0.6 | 0.6 | 0.6 |
| Associative Thickener | 1.2 | 1.2 | 1.2 | 1.2 |
| Water | 14.0 | 15.5 | 14.6 | 14.6 |
| Total Grams | 205.1 | 205.1 | 205.1 | 205.1 |

The Delta E results of the paint formulations in Table 7 are shown in FIG. 12 and the scrub resistance results of the paint formulations in Table 7 are shown in FIG. 13.

Example 15: Interior/Exterior Flat Formulation

TABLE 8

| Material | Grams | Liters | Calculated: | |
|---|---|---|---|---|
| Grind | | | | |
| Water | 222.9 | 0.223 | PVC, % | 45.6 |
| Hydroxyethylcellulose Viscosity Controller | 3.6 | 0.006 | Volume Solids. % | 38.2 |
| | | | Weight Solids, % | 63.1 |
| Copolymer Pigment Dispersant | 24.0 | 0.023 | Deco Directive VOC, g/L | 12 |
| Non-ionic surfactant/ Experimental* | 2.6 | 0.003 | Dispersant, % on pigment | 1.0 |
| Defoamer | 1.2 | 0.001 | Coalescent, % on binder solids | 4.3 |
| Biocide | 2.2 | 0.002 | | |
| Titanium Dioxide | 269.6 | 0.068 | | |
| Micronized Nepheline Syenite filler/extender | 239.7 | 0.092 | | |
| Diatomaceous Earth | 18.0 | 0.008 | | |
| Let Down | | | | |
| Prepared grind | 783.7 | 0.426 | | |
| Water | 68.3 | 0.068 | | |
| Acrylic Emulsion | 419.4 | 0.400 | | |
| Defoamer | 1.8 | 0.002 | | |
| Texanol/Optifilm 400/ Experimental* | 9.0 | 0.009 | | |
| Propylene Glycol | 12.0 | 0.012 | | |
| Hydrophobically Modified Ethylene Oxide Urethane (HEUR) Rheology Modifier | 27.0 | 0.026 | | |
| Water | 59.9 | 0.060 | | |
| Totals | 1381.0 | 1.00 | | |

*Amounts shown for Texanol control; levels varied

Figure 15:
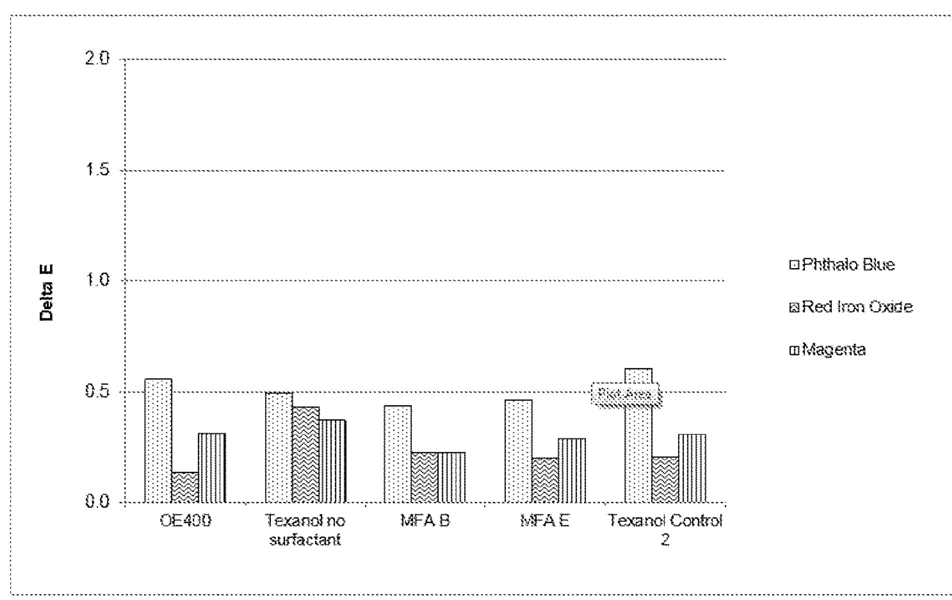

The Delta E results of the paint formulations in Table 8 are shown in FIG. 15.

Example 16: Interior Flat Formulation

TABLE 9

| Ingredients | Lbs. | Gals. |
|---|---|---|
| Grind: | | |
| Water | 445.0 | 53.45 |
| Hydroxyethylcellulose | 6.0 | 0.54 |
| Thickener | | |
| Biocide | 1.0 | 0.11 |
| Pigment Disperscent | 12.0 | 1.31 |
| Non-ionic Detergent! experimental | 2.2 | 0.25 |
| 2-amino-2-methyl-1-propanol, Co-dispersant | 2.0 | 0.25 |
| Defoamer | 2.0 | 0.26 |
| Titanium Dioxide | 100.0 | 3.13 |
| Calcined Kaolin | 150.0 | 6.80 |
| Calcium Carbonate | 150.0 | 6.61 |
| Diatomaceous Earth | 25.0 | 1.30 |
| Attapulgite Thickening Agent | 10.0 | 0.51 |
| Subtotal | 905.2 | 74.52 |
| Letdown: | | |
| Water | 46.4 | 5.57 |
| High Molecular Weight Vinyl-Acrylic Latex | 173.0 | 19.12 |
| Texanol/experimental | 4.2 | 0.53 |
| Defoamer | 2.0 | 0.26 |
| Total | 1130.8 | 100.00 |
| Properties: | | |
| Pigment Volume Concentration | 65.0% | |
| Volume Solids | 29.1% | |
| Weight Solids | 47.7% | |

Figure 16:
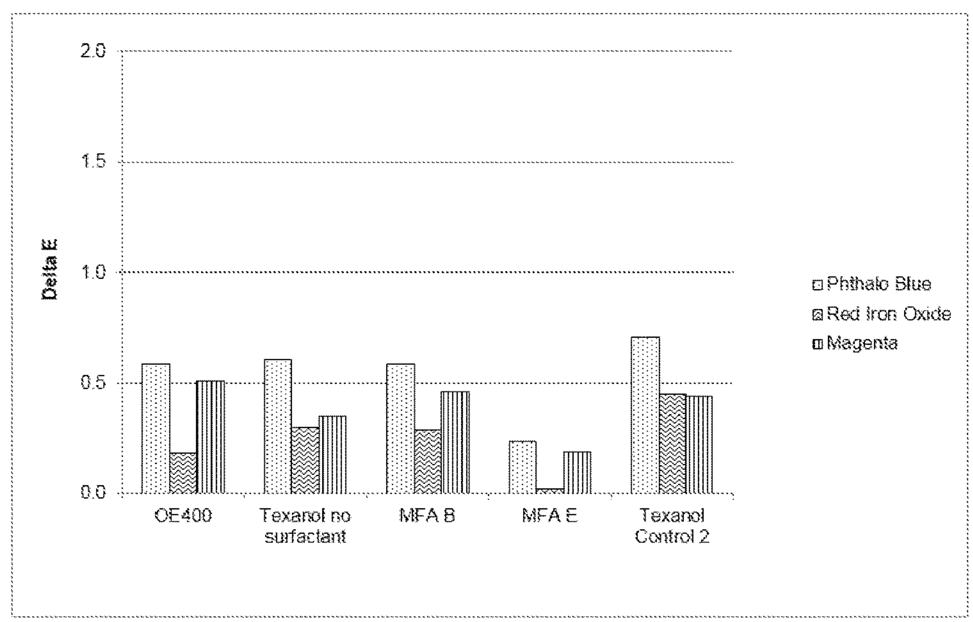

The Delta E results of the paint formulations in Table 9 are shown in FIG. 16.

Example 17: Interior Semi-Gloss Paint

TABLE 10

| Material Name | Pounds | Gallons |
|---|---|---|
| Grind | | |
| Water | 206.4 | 24.79 |
| Hydrophilic Copolymer Dispersant | 5.5 | 0.55 |
| 2-amino-2-methyl-1-propano,l Co-dispersant | 2.0 | 0.25 |
| CARBOWET 106* | 2.0 | 0.25 |
| Defoamer | 2.0 | 0.24 |
| Titanium Dioxide | 250.0 | 7.50 |
| Calcium Carbonate | 27.4 | 1.15 |
| Biocide | 1.5 | 0.18 |
| Grind Sub-total | 496.8 | 34.91 |
| Let Down | | |
| Acrylic Emulsion | 415.0 | 46.89 |
| Texanol | 14.9 | 1.89 |
| Defoamer | 2.0 | 0.12 |
| Hydrophobically Modified Ethylene Oxide Urethane (HEUR) Rheology Modifier | 21.0 | 2.41 |
| Non-ionic Urethane Rheology Modifier | 4.5 | 0.52 |
| Water | 110.4 | 13.26 |
| Totals | 1064.5 | 100.0 |
| Pigment Volume | 28.1% | |
| Concentration, % | | |
| Volume solids, % | 31.6% | |
| Weight solids, % | 46.3% | |

*CARBOWET 106 is the tradename for an ethoxylated nonionic surfactant sold by Air Products and Chemicals, Inc.

Figure 17:
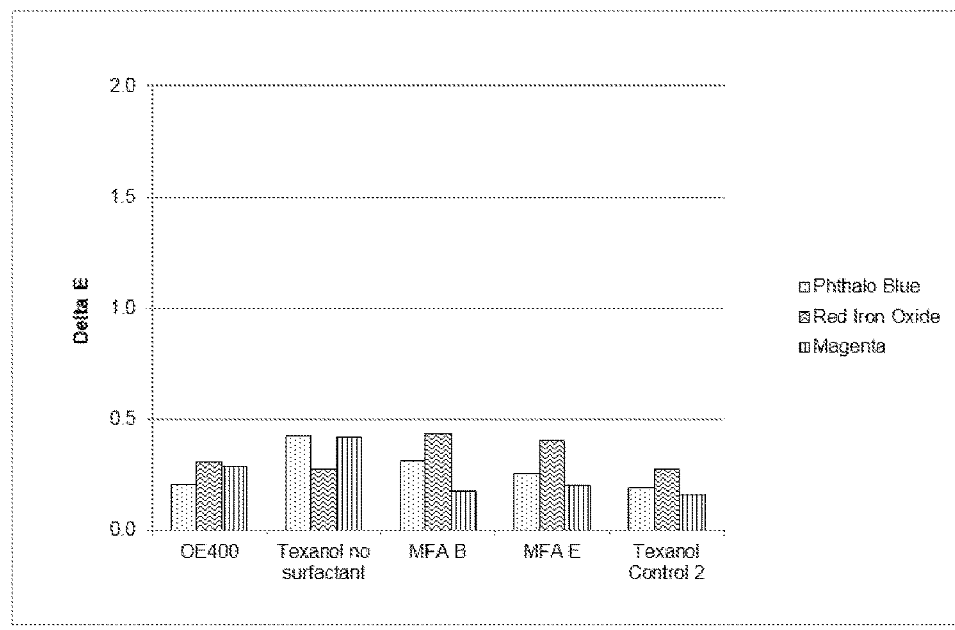

The Delta E results of the paint formulations in Table 10 are shown in FIG. 17.

The scrub resistance of the paints described in Tables 8, 9 and 10 are shown in FIG. 14.

The ethoxylate blends of this invention provide improved efficiency of $TiO_2$ compared to conventional coalescent and surfactant additives. Changes in the surfactant/wetting aid can also offer the chance for improved $TiO_2$ efficiency. The ethoxylated blends offer the same hiding and tint strength performance with a 10% or more reduction in $TiO_2$ levels by volume. These properties are shown in Examples 18-20 and Tables 11-13. Table 14 shows the formulations for the information provided in Tables 11, 12 and 13.

Example 18: Spreading Rate as Specific Contrast Ratio

TABLE 11

| | Conventional Coalescent Plus Surfactant | | | MFA SAMPLE B | | | MFA SAMPLE E | | |
|---|---|---|---|---|---|---|---|---|---|
| | Control | −10% TiO2 | −20% TiO2 | Control | −10% TiO2 | −20% TiO2 | Control | −10% TiO2 | −20% TiO2 |
| SR@99.5 CR | 5.5 | 4.0 | 3.6 | 5.0 | 5.0 | 5.5 | 5.6 | 5.9 | 4.7 |
| SR@98 CR | 7.1 | 5.9 | 5.3 | 6.7 | 6.7 | 6.9 | 7.4 | 7.4 | 6.4 |
| SR@95 CR | 10.3 | 9.6 | 8.6 | 10.0 | 10.1 | 9.7 | 11.1 | 10.4 | 10.0 |

Example 19: Whiteness Index

TABLE 12

| | Conventional Coalescent Plus Surfactant | | | MFA SAMPLE B | | | MFA SAMPLE E | | |
|---|---|---|---|---|---|---|---|---|---|
| | Control | −10% TiO2 | −20% TiO2 | Control | −10% TiO2 | −20% TiO2 | Control | −10% TiO2 | −20% TiO2 |
| Whiteness Index | 80.77 | 80.47 | 78.82 | 81.06 | 80.59 | 80.17 | 80.59 | 80.95 | 80.26 |

Example 20: Tint Strength Results (ASTM D4838-88)

TABLE 13

| | Conventional Coalescent Plus Surfactant | | | MFA SAMPLE B | | | MFA SAMPLE E | | |
|---|---|---|---|---|---|---|---|---|---|
| | Control | −10% TiO2 | −20% TiO2 | Control | −10% TiO2 | −20% TiO2 | Control | −10% TiO2 | −20% TiO2 |
| %TSAV | 100 | 99.25 | 97.05 | 100.62 | 100.91 | 98.94 | 101.81 | 101.43 | 99.11 |

| Vinyl Matt (PVC 77%) | | | | | | | | | |
|---|---|---|---|---|---|---|---|---|---|
| | Conventional Coalescent Plus Surfactant | | | MFA SAMPLE B | | | MFA SAMPLE E | | |
| Grind | Control | −10% TiO2 | −20% TiO2 | Control | −10% TiO2 | −20% TiO2 | Control | −10% TiO2 | −20% TiO2 |
| Water | 81.3 | 81.3 | 82.6 | 83.0 | 83.6 | 84.1 | 83.1 | 83.7 | 84.2 |
| Non-ionic, Low Viscosity, Water Soluble Cellulose Ether | 2.5 | 2.5 | 2.5 | 2.5 | 2.5 | 2.5 | 2.5 | 2.5 | 2.5 |
| Coalescent Neutralization Amine | 2.2 | 2.2 | 2.2 | 2.2 | 2.2 | 2.2 | 2.2 | 2.2 | 2.2 |
| Defoamer | 0.9 | 0.9 | 0.9 | 0.9 | 0.9 | 0.9 | 0.9 | 0.9 | 0.9 |
| Phenol-free Nonionic Wetting agent and Emulsifier | 2.2 | 2.2 | 2.2 | 0.0 | 0.0 | 0.0 | 0.0 | 0.0 | 0.0 |
| MFA Sample B | 0.0 | 0.0 | 0.0 | 1.1 | 1.1 | 1.1 | 0.0 | 0.0 | 0.0 |
| MFA Sample E | 0.0 | 0.0 | 0.0 | 0.0 | 0.0 | 0.0 | 1.0 | 1.0 | 1.0 |

-continued

| Vinyl Matt (PVC 77%) | | | | | | | | | |
|---|---|---|---|---|---|---|---|---|---|
| | Conventional Coalescent Plus Surfactant | | | MFA SAMPLE B | | | MFA SAMPLE E | | |
| Grind | Control | −10% TiO2 | −20% TiO2 | Control | −10% TiO2 | −20% TiO2 | Control | −10% TiO2 | −20% TiO2 |
| Hydrophilic Copolymer Dispersant | 1.5 | 1.5 | 1.5 | 1.5 | 1.5 | 1.5 | 1.5 | 1.5 | 1.5 |
| Biocide | 0.8 | 0.8 | 0.8 | 0.8 | 0.8 | 0.8 | 0.8 | 0.8 | 0.8 |
| Dolomite Powder | 26.1 | 26.9 | 27.8 | 26.6 | 27.6 | 28.6 | 26.6 | 27.6 | 28.6 |
| Talc | 15.2 | 15.3 | 15.6 | 15.5 | 15.6 | 16.0 | 15.5 | 15.7 | 16.0 |
| Calcined Kaolin | 30.4 | 31.0 | 31.7 | 31.0 | 31.8 | 32.6 | 31.0 | 31.8 | 32.7 |
| Chloride-Process Rutile Titanium Dioxide Pigment | 34.8 | 31.3 | 27.9 | 35.4 | 32.1 | 28.7 | 35.5 | 32.2 | 28.4 |
| Letdown | | | | | | | | | |
| APEO-Free Anionic Styrene Acrylic Binder | 40.0 | 40.0 | 40.7 | 40.7 | 41.0 | 41.3 | 40.8 | 41.1 | 41.3 |
| Texanol | 1.4 | 1.4 | 1.4 | 0.0 | 0.0 | 0.0 | 0.0 | 0.0 | 0.0 |
| MFA Sample B | 0.0 | 0.0 | 0.0 | 1.1 | 1.1 | 1.1 | 0.0 | 0.0 | 0.0 |
| MFA Sample E | 0.0 | 0.0 | 0.0 | 0.0 | 0.0 | 0.0 | 0.9 | 1.0 | 1.0 |
| Hydrophobically Modified Anionic Thickener | 1.9 | 1.9 | 1.9 | 1.9 | 1.9 | 1.9 | 1.9 | 1.9 | 1.9 |
| Defoamer | 0.9 | 0.9 | 0.9 | 0.9 | 0.9 | 0.9 | 0.9 | 0.9 | 0.9 |
| Coalescent Neutralization Amine | 0.6 | 0.6 | 0.6 | 0.6 | 0.6 | 0.6 | 0.6 | 0.6 | 0.6 |
| Water | 57.4 | 57.4 | 58.4 | 54.0 | 54.4 | 54.8 | 54.1 | 54.5 | 54.8 |
| Total | 300 | 300 | 300 | 300 | 300 | 300 | 300 | 300 | 300 |

The invention has been described in detail with particular reference to preferred embodiments thereof, but it will be understood that variations and modifications can be effected within the spirit and scope of the invention.

We claim:

1. A coalescent and non-ionic surfactant blend comprising:

a) structure (1);

(1)

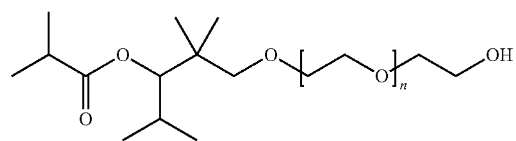

b) structure (2); and (2)

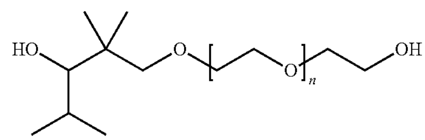

c) structure (3);

(3)

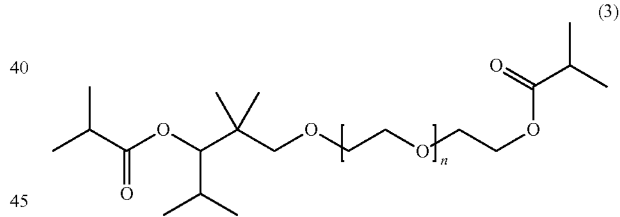

wherein n is 1 to 5.

2. The coalescent and non-ionic surfactant blend of claim 1 further comprising a mixture of 2,2,4-trimethyl-1,3-pentanediol monoisobutyrate, di-isopropyl ketone, isobutyl isobutyrate, isobutanol, and 2-isobutoxy-ethanol.

3. A composition derived by reacting 2,2,4-trimethyl-1,3-pentanediol monoisobutyrate (TXOL) with ethylene oxide in the presence of a catalyst, at temperatures of from about 100° to 200° C., and under pressures of from about 345 kPa to 1800 kPa and separating ethoxylatedstructures (1), (2) and (3) from the reaction mixture:

(1)

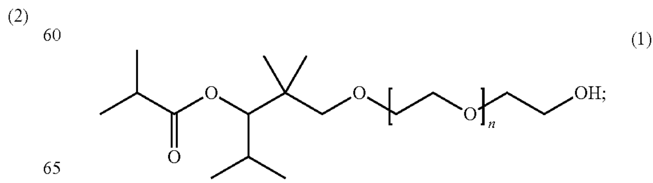

(2)

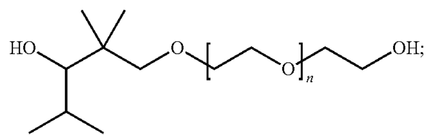

(3)

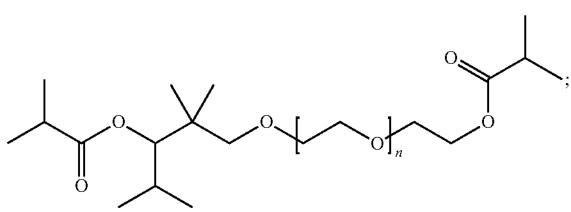

wherein n is 1 to 5.

4. A coating composition comprising:

A. at least one latex compound;

B. at least one pigment;

C. a coalescent and non-ionic surfactant blend comprising:

a) 10 to 60 weight percent structure (1);

(1)

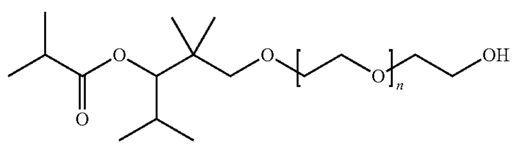

b) 5 to 50 weight percent structure (2);

(2)

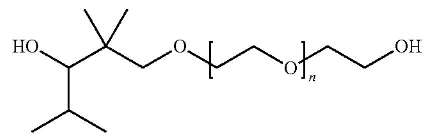

c) 0 to 30 weight percent structure (3); and (3)

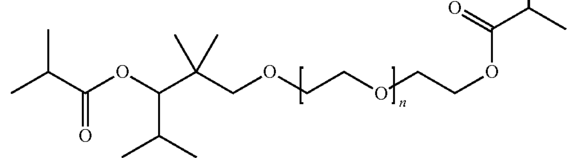

based on the total weight of said coalescent and non-ionic surfactant mixture and wherein n is 1 to 5.

5. The coating composition of claim 4 wherein said latex compound is selected from the group comprising acrylic latex, vinyl acrylic latex, vinyl versatate vinyl acrylics latex, ethylene vinyl acetate latex, and styrene acrylic latex.

6. The coating composition of claim 4 wherein said pigment is $TiO_2$, calcium carbonate, talc, silica, nepheline syenite, or clay.

7. A coalescent and non-ionic surfactant blend for use in aqueous architectural coatings comprising:

a) 10 to 60 weight percent structure (1);

(1)

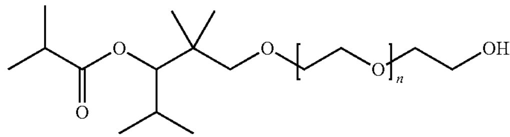

b) 5 to 50 weight percent structure (2);

(2)

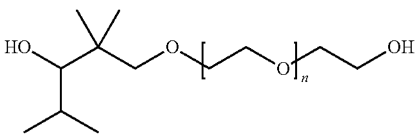

c) 0 to 30 weight percent structure (3); and (3)

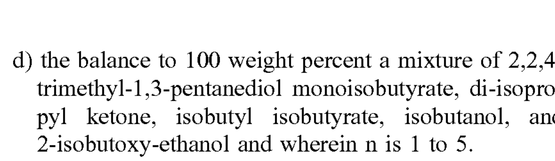

d) the balance to 100 weight percent a mixture of 2,2,4-trimethyl-1,3-pentanediol monoisobutyrate, di-isopropyl ketone, isobutyl isobutyrate, isobutanol, and 2-isobutoxy-ethanol and wherein n is 1 to 5.

* * * * *